(12) United States Patent
Härmä et al.

(10) Patent No.: US 11,752,288 B2
(45) Date of Patent: Sep. 12, 2023

(54) SPEECH-BASED BREATHING PREDICTION

(71) Applicant: KONINKLIJKE PHILIPS N.V., Eindhoven (NL)

(72) Inventors: Aki Sakari Härmä, Eindhoven (NL); Francesco Vicario, Boston, MA (US); Venkata Srikanth Nallanthighal, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 562 days.

(21) Appl. No.: 17/071,312

(22) Filed: Oct. 15, 2020

(65) Prior Publication Data

US 2021/0146082 A1    May 20, 2021

Related U.S. Application Data

(60) Provisional application No. 62/936,811, filed on Nov. 18, 2019.

(51) Int. Cl.
*A61M 16/00* (2006.01)
*G10L 15/06* (2013.01)
*G10L 15/16* (2006.01)

(52) U.S. Cl.
CPC ...... *A61M 16/026* (2017.08); *A61M 16/0003* (2014.02); *G10L 15/063* (2013.01); *G10L 15/16* (2013.01); *A61M 2016/0021* (2013.01); *A61M 2205/50* (2013.01); *A61M 2230/42* (2013.01)

(58) Field of Classification Search
CPC ............ A61M 16/026; A61M 16/0003; A61M 2016/0021; A61M 2205/50; A61M 2230/42; G10L 15/063; G10L 15/16
See application file for complete search history.

(56) References Cited

U.S. PATENT DOCUMENTS

| 5,806,515 | A | 9/1998 | Bare et al. |
| 9,956,363 | B2 | 5/2018 | Masic |
| 10,232,136 | B2 | 3/2019 | Aguirre et al. |
| 2007/0144518 | A1 | 6/2007 | Acker et al. |
| 2009/0205662 | A1* | 8/2009 | Kwok ................. A61M 16/024 128/204.23 |
| 2015/0202395 | A1 | 7/2015 | Fromentin |

(Continued)

FOREIGN PATENT DOCUMENTS

WO    2014045257 A1    3/2014

OTHER PUBLICATIONS

International Search Report for PCT/EP2020/082311 dated Nov. 17, 2020.

(Continued)

*Primary Examiner* — Steven O Douglas
(74) *Attorney, Agent, or Firm* — Daniel H. Brean (57) ABSTRACT

In an embodiment, a method is described. The method comprises obtaining an indication of a speech pattern of a subject and using the indication to determine a predicted time of inspiration by the subject. A machine learning model is used for predicting the relationship between the speech pattern and a breathing pattern of the subject. The machine learning model can then be used to determine the predicted time of inspiration by the subject. The method further comprises controlling delivery of gas to the subject based on the predicted time of inspiration by the subject.

15 Claims, 5 Drawing Sheets

(56) References Cited

U.S. PATENT DOCUMENTS

2017/0296094 A1 10/2017 Fleming et al.
2019/0224431 A1 7/2019 Barnes et al.

OTHER PUBLICATIONS

Anonymous: "Recurrent neural network—Wikipedia". Jun. 5, 2018.
Fairbanks, G. "Rainbow Passage. Voice and articulation drillbook". 2nd edn. p. 124-139, 1960.

* cited by examiner

SPEECH-BASED BREATHING PREDICTION

CROSS-REFERENCE TO RELATED APPLICATIONS

This patent application claims the priority benefit under 35 U.S.C. § 119(e) of U.S. Provisional Application No. 62/936,811 filed on Nov. 18, 2019, the contents of which are herein incorporated by reference.

TECHNICAL FIELD OF THE INVENTION

The invention relates to a method, apparatus and tangible machine-readable medium for controlling, for example, delivery of gas to a subject such as a patient.

BACKGROUND OF THE INVENTION

A subject such as a respiratory patient may have a need for supportive therapy for various respiratory ailments such as Chronic Obstructive Pulmonary Disease, COPD. Respiratory support for such ailments may be provided by a ventilation system for delivering gas such as therapy air to the subject. The ventilation system may deliver the therapy air to the subject with a certain oxygen level and/or pressure selected for the subject's individual therapy requirements. This therapy air may be administered using an interface such as a nasal cannula or a mouth and/or nose mask. In some cases, the delivery of therapy air may be driven by sensing spontaneous breathing attempts by the subject.

Lungs are needed for both speech and respiration which, in the case of respiratory patients, may lead to difficulties in terms of social interactions related to disturbed speech and/or health problems due to disrupted gas exchange during speech.

A subject's breathing rate may typically be significantly lower during speech than when the subject is not speaking. For example, in healthy subjects the respiration rate may slow down by 50% during speech. Since expiration takes place during speech and inspiration is mostly performed in pauses of speech, the breathing pattern may be asymmetrical since a healthy subject may take short inspirations and relatively long expirations during speech. As a consequence, respiration may be impaired during speech. The corresponding, temporary increase in carbon dioxide levels and decrease in oxygen levels in the lung is typically not a problem for healthy subjects but may cause discomfort in certain respiratory patients. A respiratory patient may need additional support (e.g., more oxygen) during speech. However, a ventilation system for providing respiratory support to the patient may be less effective or efficient at providing such support during speech, for example, due to the slower breathing rate and/or the relatively long expiration periods associated with speech. Further, attempting to directly monitor the breathing pattern of the subject may involve use of additional equipment which may place additional burden on the subject in terms of setting up and using the additional equipment.

Accordingly, an object is to improve support provided to a subject in receipt of gas during speech. Another object is to improve the performance of gas delivery to a subject during speech.

SUMMARY OF THE INVENTION

Aspects or embodiments described herein relate to improving support provided to a subject in receipt of gas during speech and/or improving gas delivery to a subject during speech. Aspects or embodiments described herein may obviate one or more problems associated with supporting a subject during speech and/or delivering gas to a subject during speech.

In a first aspect, a method is described. The method comprises obtaining an indication of a speech pattern of a subject. The method further comprises using the indication to determine a predicted time of inspiration by the subject. The determination is performed by processing circuitry. The determination is based on a machine learning model for predicting a relationship between the speech pattern and a breathing pattern of the subject. The method further comprises controlling delivery of gas to the subject based on the predicted time of inspiration by the subject.

In some embodiments, the method comprises deriving a respiration signal from the indication and using the respiration signal as an input to the machine learning model to predict, (e.g., using the processing circuitry), the time of inspiration by the subject.

In some embodiments, the machine learning model is built using a neural network configured to identify any correlations between a speech signal and a corresponding respiration signal acquired from a plurality of trainers.

In some embodiments, the neural network is configured to identify at least one of: linguistic content and prosodic features of speech signals acquired from the trainers to facilitate identification of the correlation.

In some embodiments, the method comprises causing a ventilation system to deliver the gas to the subject during the predicted time of inspiration for a specified period of time. The specified period of time may be one of: a pre-determined period of time; or adapted according to the subject's individual needs.

In some embodiments, the subject's individual needs are determined based on at least one of: linguistic context of the subject's speech; previous inspiration durations by the subject; and a medical need of the subject.

In some embodiments, the method comprises using change-point detection to predict the time of inspiration of the subject based on the subject's respiration signal as predicted by the machine learning model based on the speech pattern of the subject.

In a second aspect, apparatus is described. The apparatus comprises processing circuitry. The processing circuitry comprises a prediction module. The prediction module is configured to use an indication of a speech pattern of a monitored subject to determine a predicted time of inspiration by the subject. The determination is based on a machine learning model for predicting a relationship between the speech pattern and a breathing pattern of the subject. The processing circuitry further comprises a control module. The control module is configured to control delivery of gas to the subject based on the predicted time of inspiration by the subject.

In some embodiments, the apparatus comprises a sound transducer configured to obtain a speech signal corresponding to the speech pattern of the subject.

In a third aspect, a tangible machine-readable medium is described. The tangible machine-readable medium stores instructions which, when executed by at least one processor, cause the at least one processor to determine, from an indication of a speech pattern of a subject, a predicted time of inspiration by the subject. The determination is based on a machine learning model for predicting a relationship between the speech pattern and a breathing pattern of the subject. The instructions further cause the at least one processor to control delivery of gas to the subject based on the predicted time of inspiration by the subject.

In some embodiments, the machine learning model is trained with a plurality of speech signals and corresponding respiration signals acquired from a plurality of trainers.

In some embodiments, an input to the machine learning model comprises a spectral representation of the plurality of speech signals; and an indication of the corresponding respiration signals at specified time intervals. The input may be fed into a neural network comprising a plurality of memory layers such that, when the neural network is optimized to update network weighting based on the input, the machine learning model may be updated accordingly.

In some embodiments, the spectral representation of each of the plurality of speech signals is obtained. In an embodiment, the spectral representation is obtained by filtering each speech signal to spectrally flatten the speech signal and boost higher frequencies compared with lower frequencies of the speech signal; applying a Fourier transform to obtain a power spectrum corresponding to the speech signal; applying a Mel-frequency scaling to the power spectrum to obtain a Mel spectrogram; and selecting a plurality of time windows from the Mel spectrogram, wherein each time window is separated by a specified stride interval. The indication of the corresponding respiration signals at specified time intervals is obtained by: obtaining a respiratory inductive plethysmography, RIP, signal from the training subject; and determining an RIP signal value at the end of each time window within the specified stride interval.

In some embodiments, the neural network comprises at least one of: a recurrent neural network, RNN; an RNN-long short term memory, RNN-LSTM, network; and a convolutional neural network, CNN.

In some embodiments, an attention mechanism with breathing rate as an auxiliary training parameter is used to optimize the neural network.

Aspects or embodiments described herein may provide improved support to a subject in receipt of gas during speech and/or may improve the performance of gas delivery to a subject during speech. For example, the aspects or embodiments described herein may provide improved delivery of gas to the subject to support the subject's speech and/or may provide improved gas delivery to the subject to support respiration during speech.

These and other aspects of the invention will be apparent from and elucidated with reference to the embodiment(s) described hereinafter.

BRIEF DESCRIPTION OF DRAWINGS

Exemplary embodiments of the invention will now be described, by way of embodiment only, with reference to the following drawings, in which.

DETAILED DESCRIPTION OF THE EMBODIMENTS

Figure 1:
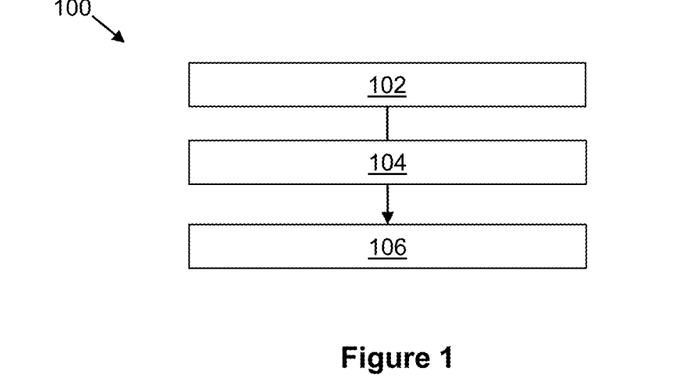
FIG. 1 refers to a method of controlling delivery of gas according to an embodiment.

FIG. 1 shows a method 100 (e.g., a computer-implemented method) of controlling delivery of gas such as therapy air to a subject such as a respiratory patient. The method 100 may be used to control the supply of gas provided by a ventilation system (an example of which is described in more detail below in relation to FIGS. 2a to 2b). For example, the method 100 may provide an instruction or other indication to the ventilation system to control the manner by which the ventilation system delivers the gas. For example, the timing and/or duration of the gas delivery may by controlled based on the instruction or other indication provided by the method 100.

The method 100 comprises obtaining, at block 102, an indication of a speech pattern of a subject. The speech pattern of the subject may be obtained from a sound transducer such as a microphone for detecting sound and generating a signal representative of the detected sound. The speech pattern may comprise characteristic features such as prosodic features and/or linguistic content which may be present in the signal generated by the sound transducer.

The method 100 comprises using the indication to determine (e.g., using processing circuitry), at block 104, a predicted time of inspiration by the subject based on a machine learning model for predicting a relationship between the speech pattern and a breathing pattern of the subject.

A breathing pattern has two phases: inspiration (i.e., breathing in) and expiration (i.e., breathing out). The breathing pattern may be adapted (either voluntarily or involuntarily) by the subject according to the subject's speech pattern. The speech pattern of the subject may comprise characteristic features (e.g., prosodic features and/or linguistic content) which may be indicative of whether the subject is inspiring or expiring. For example, a pause in speech may be indicative that the subject is inspiring or about to inspire. A change in pitch or speed of the speech may be indicative that a subject has just inspired or is about to inspire. A subject's speech may comprise sentences during which the subject may expire and between which the subject may inspire. These are just a few examples of how certain characteristic features of the speech pattern may relate to the breathing pattern of the subject.

In reality, speech patterns can be complex and vary (e.g., during a subject's speech or between different subjects) such that it is difficult to design a reliable model for predicting the relationship between a subject's speech pattern and their breathing pattern. The above examples of how a subject's breathing pattern may depend on the subject's speech pattern are merely illustrative assumptions of how a subject's breathing pattern may be related to the subject's speech pattern and should not be regarded as a definitive due to complexity and/or variability in a subject's speech and breathing pattern.

It may be possible to detect the pauses in speech and inspiration attempts by the subject, for example, by monitoring signals generated by an air flow sensor, air pressure sensor and/or a microphone. However, the duration of inspiration in normal speech may typically last for a few hundred milliseconds, which may be too fast for certain ventilators (e.g., mechanical ventilators) to react within a sufficiently short timeframe to deliver gas once an inspiration attempt has been detected. For example, a ventilator providing gas via an interface such as a nasal cannula connected to ventilator via a hose may take a specified amount of time to deliver the gas that depends on the length of the hose (and the reaction speed of the ventilator) upon receiving an indication that the ventilator is to deliver the gas. For moments of inspiration with a duration of, for example, a few hundred milliseconds, the subject may receive the gas too late to be adequately supported by the ventilation system during speech. Also, speech may create artifacts in air pressure and flow signals that may create difficulties in terms of detecting actual breaths. In addition, the moment of inspiration may depend on what the subject is trying to say, the linguistic content and/or the context of the speech. Thus, attempting to detect pauses in speech and inspiration attempts directly based on sensor data such as provided by an air flow sensor, air pressure sensor and/or a microphone may not necessarily enable a ventilation system to provide adequate support to a subject during speech.

The machine learning model referred to in the method 100 may be used to interpret the subject's speech pattern such that it may be possible to predict the subject's breathing pattern with an acceptable reliability. The machine learning model may be used to interpret the complex and/or variable patterns in the speech pattern of the subject in order to provide the prediction of the subject's breathing pattern. As will be described in greater detail herein, the machine learning model may be trained using information from a training data set derived from the speech and breathing patterns obtained from a plurality of human trainers. This machine learning approach may provide a simplified way to model speech and breathing patterns without having to construct a model that relies on certain assumptions (such as the illustrative assumptions described above) which may otherwise yield erroneous predictions due to potential bias and/or errors in the assumptions. Since the machine learning model may avoid making or may reduce its reliance on certain assumptions, predictions that are based on the machine learning model may be more reliable than a model that relies on assumptions that could otherwise be subject to bias and/or erroneous.

The method 100 further comprises controlling, at block 106, delivery of gas to the subject based on the predicted time of inspiration by the subject. For example, the method 100 may generate an indication (e.g., an inspiration signal) that may be received by a ventilator of a ventilation system to cause the ventilator to deliver the gas to the subject based on the predicted time of inspiration.

Since the machine learning model may be used to provide a prediction of the time of inspiration by the subject during speech (for example, the start point and/or duration of the inspiration attempt), the method 100 may trigger the delivery of gas by a ventilation system for the predicted time of inspiration. For example, where the ventilation system has a specified reaction time (e.g., due to the reaction speed of the ventilator and/or length of the hose connecting the ventilator and the interface), the prediction may trigger the delivery of gas in time to provide sufficient support to a subject in receipt of gas during speech. In other words, the machine learning model may allow the method 100 to proactively predict a time of inspiration based on a subject's speech pattern, which may provide sufficient time for the ventilation system to react to deliver the gas within a specified timeframe and/or allow the ventilation system to deliver gas for a duration of time corresponding to the duration of inspiration by the subject. Further, an end-user of a ventilation system (such as the subject themselves) may find setting up the ventilation system relatively straightforward since the method 100 may reduce or avoid the need for additional equipment such as body sensors for directly monitoring respiration. Configuring a ventilation system to include monitoring speech data (e.g., using a microphone or other sound detector) may be regarded as relatively straightforward for an end-user to set up themselves.

Figure 2A:
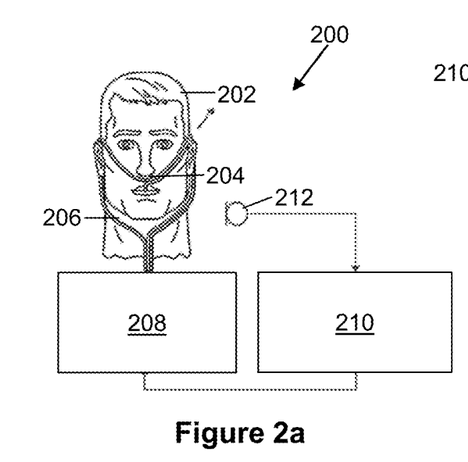
FIGS. 2a to 2b are schematic drawings of a ventilation system according to an embodiment.

FIG. 2a schematically depicts a ventilation system 200 according to an embodiment for at least partially implementing certain methods described herein, such as the method 100 of FIG. 1. In FIG. 2a, a subject 202 is fitted with an interface which, in this embodiment, comprises a nasal cannula 204 for delivering gas to the subject 202 via a hose 206 connected to a ventilator 208. The ventilator 208 may be controlled (e.g., according to block 106 of the method 100) such that certain gas parameters (e.g., gas flow rate, pressure, oxygen level, timing and/or any other parameters relevant to the delivery of the gas) are appropriate for the subject's needs at a particular moment in time.

In this regard, the ventilation system 200 further comprises a prediction module 210 for at least partially implementing certain methods described herein. For example, the prediction module 210 may implement at least one of: blocks 102, 104 and 106 of the method 100. An input 212 to the prediction module 210 may provide the speech pattern of the subject 202 to the prediction module 210. Upon receiving a speech pattern from the input 212, the prediction module 210 may predict the time of inspiration by the subject 202. This predicted time of inspiration may be used to control delivery of the gas to the subject 202.

Figure 2B:
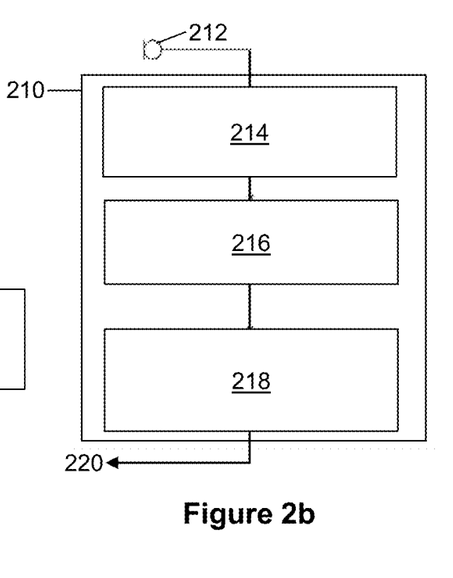

FIG. 2b schematically depicts certain modules of the prediction module 210. In this embodiment and as described in more detail below, the prediction module 210 comprises a pre-processing module 214 for converting the monitored speech into a format appropriate for being input to a machine learning module 216 that outputs a prediction of the subject's breathing pattern (i.e., their anticipated breathing pattern based on the monitored speech pattern). In this embodiment, the machine learning module 216 comprises a deep recurrent neural network although other types of neural networks or machine learning models may be used. Based on the predicted breathing pattern (e.g., a 'predicted respiratory wave') generated by the machine learning module 216, an inspiration prediction module 218 may predict the time of inspiration by the subject 202 and generate a ventilator control signal 220 for causing the ventilator 208 to deliver gas to the subject for the predicted time of inspiration by the subject 202.

The ventilator control signal 220 may cause the activation of the ventilator 208 at the beginning of the predicted inspiration such that gas can flow to the lungs of the subject 202 (e.g., by the subject 202 inhaling the gas or by the gas being forced in by a gas pump). The amount (e.g., concentration or rate) of oxygen and/or pressure may also be adjusted according to the detected and/or predicted respiration rate, to compensate for reduced minute ventilation and/or prevent the shortness of breath, hypoxemia, and/or hypercapnia. At the end of the predicted inspiration, the ventilator control signal 220 may cause the deactivation of the ventilator 208 to stop the flow of gas and thus allow the subject 202 to breathe out.

An output of the machine learning model (i.e., using the machine learning module 210) may be indicative of an estimated, or predicted, respiration signal. In an embodiment, a change-point detection algorithm (e.g., implemented by the inspiration prediction module 218) uses the estimated respiration signal to predict the inspiration moments of the subject 202. In an embodiment, a pump of the ventilator 208 may be switched on a short time T (e.g., T=300 milliseconds) before the expected (i.e., predicted) start of inspiration such that gas is delivered to the subject 202 in time for inspiration. In an embodiment, the value of T may be optimized individually for each subject 202 (e.g., depending on, for example, the capability of the ventilator 208, a preferred mode of ventilator 208 operation and/or individual requirements of the subject 202). The value of T may depend on the linguistic context of the speech and/or may be based on inspiration pause durations observed previously. In an embodiment, the duration of ventilation may be based on data from the individual subject 202 and/or the context of the subject's 202 speech. Thus, in some embodiments, the value of T may be at least one of: pre-determined; selected based on analysis of the subject's speech and/or selected based on previous predictions of the subject's respiration signal.

Figure 3:
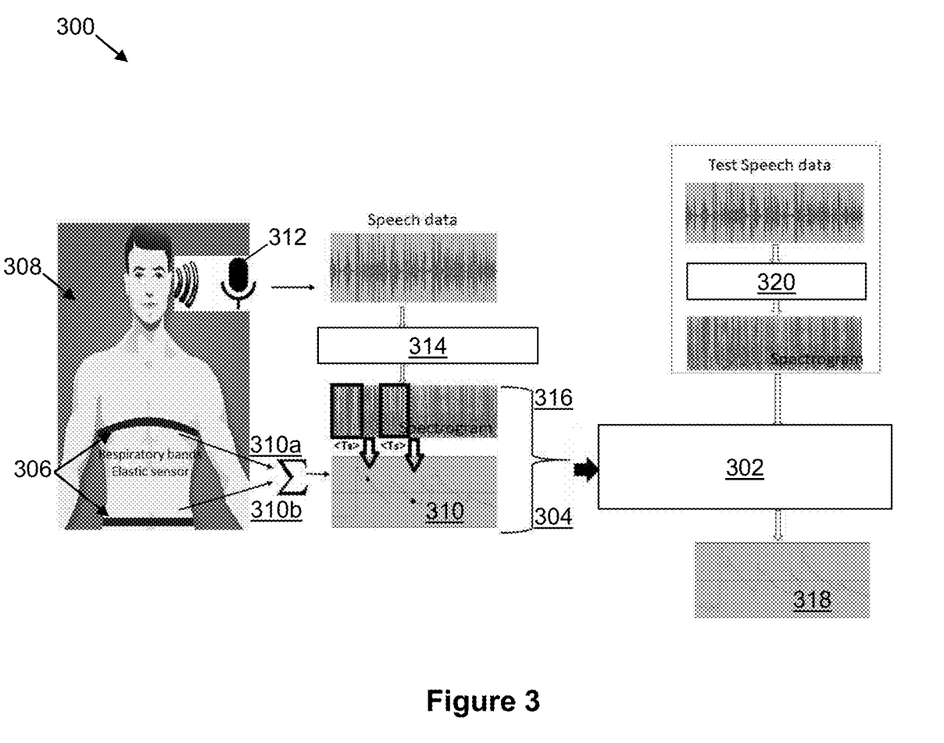
FIG. 3 is a schematic drawing of a system for training and testing a machine learning model according to an embodiment.

FIG. 3 schematically depicts a system 300 according to an embodiment for training (and subsequently testing) a machine learning model 302 for predicting a breathing pattern of a subject based on the subject's speech. The machine learning model 302 may be implemented by a machine learning module 216 such as described in relation to FIG. 2b. As will be described in greater detail below, in some embodiments, the machine learning model 302 is based on a deep recurrent neural network or other sequential regression algorithm. The machine learning model 302 is trained with a large amount of speech and respiration data where the trainer's respiration data is collected, for example, using an air flow measurement sensor and/or a body sensor. In the embodiment of FIG. 3, a training respiration signal 304 (i.e., a 'measured breathing pattern') is collected by a body sensor which, in this embodiment, comprises two respiratory elastic band sensors 306 arranged to monitor chest and/or abdomen movement of a trainer 308 during respiration. The training respiration signal 304 may be indicative of a respiratory inductive plethysmography, RIP, signal. In this embodiment, one of the sensors 306 is placed around the ribcage of the trainer 308 while the other of the sensors 306 is placed around the abdomen of the trainer 308 although a different number of sensors (e.g., one or three or more) may be used and positioned as appropriate to detect chest and/or abdomen movements corresponding to the trainer's 308 respiration. As the trainer 308 respires, the movement of their chest and/or abdomen causes at least one of the respiratory elastic band sensors 306 to expand and/or contract to generate body movement signals 310 (e.g., a ribcage signal 310a and an abdomen signal 310b) which are collectively indicative (e.g., by combining the body movement signals 310) of the training respiration signal 304.

In this embodiment, the speech of the trainer 308 is detected using a microphone 312 although any other device for detecting speech may be used instead of or as well as the microphone 312. The microphone 312 generates speech data based on the trainer's 308 speech which is processed by a training speech processing module 314 (which may correspond to the 'pre-processing module 214' as described in relation to FIG. 2) into training speech signal data 316 for input to the machine learning model 302. The training speech processing module 314 performs audio spectral analysis to convert the speech data (as monitored by the microphone 312) into a format appropriate for input to the machine learning model 302.

In this embodiment, the processing of the speech data is performed as follows using the indicated values. The training speech signal data 316 is split into fixed time window lengths of 4 seconds with a stride of 10 milliseconds between adjacent windows (in FIG. 3, these windows are indicated by boxes with a window length '<Ts>' and the stride is exaggerated in length for ease of understanding). These windows of speech signal data 316 are processed by a filter (e.g., a pre-emphasis filter) to spectrally flatten the speech signals and boost higher frequencies. A Short-Time Fourier Transform, STFT, is computed with a short frame size of 25 milliseconds, a stride of 10 milliseconds and a hamming window to obtain the power spectrum. Mel filter banks (in this embodiment n=40 Mel filter banks) are applied to the power spectrum to obtain the Mel spectrum. Mel filter banks apply Mel-frequency scaling, which is a perceptual scale that helps to simulate the way the human ear and brain works to interpret sound. The Mel spectrum may provide better resolution at low frequencies and less resolution at relatively higher frequencies. A Log Mel spectrogram is then generated to represent the spectral features of the training speech signal data 316 as an input to the machine learning model 302. In other embodiments, different values may be used (e.g., different window lengths, strides and frame lengths) when processing the speech data to generate the Log Mel spectrogram.

In order to determine the training respiration signal 304 to be used as another input to the machine learning model 302, the Log Mel spectrogram is mapped with the training respiration signal 304 at the endpoint of the time window to train the model 302 with a stride of 10 milliseconds between windows. As shown by FIG. 3, each time window of the Log Mel spectrogram is fed into the machine learning model 302 while the corresponding respiration signal 304 at the endpoint of these time windows is also fed into the machine learning model 302.

Thus, the input training data for training of the machine learning model 302 is based on a spectral representation of speech and samples of the training respiration signal from each trainer 308 during conversations. Each trainer 308 is healthy (i.e., they do not have a respiratory ailment) and a plurality of the trainers 308 are used to train the machine learning model 302. In an example training session, forty (40) trainers 308 were instructed to read a phonetically balanced paragraph. In this example, the phonetically balanced paragraph read by the trainers 308 is known as the "Rainbow Passage" (from Fairbanks, G. (1960). Voice and articulation drillbook, 2nd edn. New York: Harper & Row. pp 124-139), a commonly-used paragraph for speech training purposes.

In this embodiment, the machine learning model 302 is based on a Recurrent Neural Network-Long Short Term Memory, RNN-LSTM, network model. In the RNN-LSTM network model, the input training data is fed into a network of two long short term memory layers with 128 hidden units and a learning rate of 0.001. An Adam optimizer is used as an optimization algorithm to update network weights iteratively based on the input training data. Mean squared error is used as the regression loss function. The hyperparameters selected for the network are estimated after repeated experimentation although could instead be randomly selected.

Figure 4:
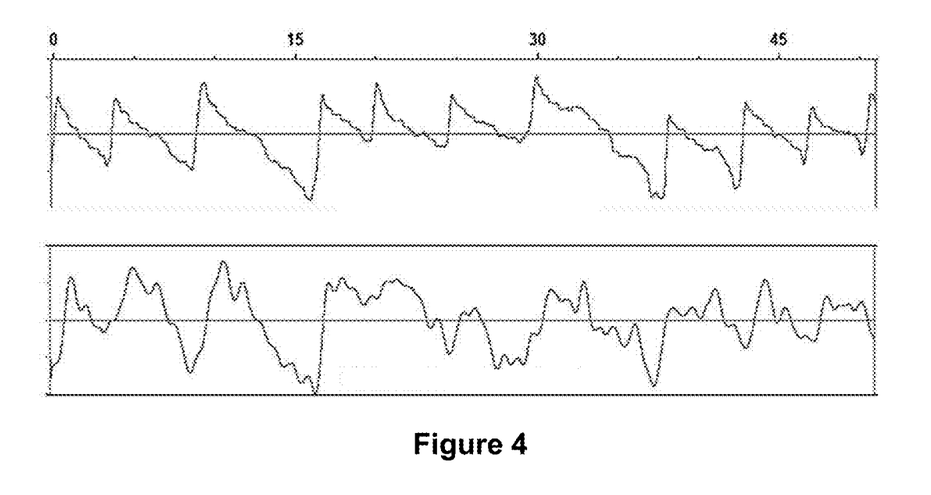
FIG. 4 is a graph of experimental results from testing the machine learning model referred to in FIG. 3.

FIG. 4 is a graph depicting the experimental results of a test run using the trained model 302 to estimate the respiratory signal 318 (i.e., the 'estimated breathing pattern' or 'estimated breathing signal') of a test subject to cross-validate (e.g., using 'leave one subject' cross validation) the data from the plurality of trainers 308. Accordingly, each test subject's speech data was processed in the same way as the training speech data from the remaining trainers 308 e.g., using a test speech processing module 320 which may provide the same functionality as the training speech processing module 314. FIG. 4 shows an example comparison between the measured (or 'actual') breathing signal (e.g., an 'RIP signal') in the upper graph and the estimated breathing signal (i.e., the estimated, or predicted, respiratory signal 318) in the lower graph as a function of time (in seconds) for a test subject.

Since estimating a breathing pattern from speech data using the RNN-LSTM network model is a regression problem, two metrics are used for evaluation and comparison of the measured and estimated breathing signals. These metrics are correlation and mean squared error, MSE, of the estimated breathing signal and the measured breathing signal. Accordingly, experimental results produced by the model which provide a high correlation value and/or a low MSE may be indicative that the trained model may provide an acceptable or reliable estimation of the breathing signal. For example, the experimental results from a test subject depicted by FIG. 4 were found to estimate the breathing pattern of the test subject with a correlation of 0.42 and MSE of 0.0016 to the test subject's measured respiratory signal. By way of example, another test subject's experimental results were found to estimate the test subject's breathing pattern with a correlation of 0.47 and an MSE of 0.0017.

Based on the training and testing of the model 302, it was observed that a trainer's breathing rate during conversational speech is nearly half their normal breathing rate (i.e., as compared to their breathing rate when not speaking). Certain breathing parameters such as breathing rate and tidal volume were determined for the plurality of trainers 308 based on their experimental results. As such, for the plurality of trainers 308, an average estimated breathing rate of 7.9 breaths per minute with an error of 5.6% was observed. Further, the tidal volume was estimated with an error of 2.4%. As can be recognized from FIG. 4, certain breathing events (such as the points of inhalation and expiration as well as the lengths thereof) may be apparent from the estimated and measured breathing signals. In order to determine certain breathing events (e.g., the point of inhalation), an algorithm (e.g., a 'change-point detection algorithm') for identifying peaks and/or troughs of the estimated breathing signal may be implemented. Thus, where the algorithm detects a change that appears to correspond to a certain breathing event, this may be compared to the measured breathing signal to determine whether or not the detected change does indeed correspond to the breathing event. Based on the experimental results from the plurality of trainers 308, the inhalation events were identified with a sensitivity of 0.88, precision of 0.82 and an F1 score of 0.8534.

Experimental results based on the above experimentation demonstrate that the RNN-LSTM network model may be capable of learning and understanding the dynamics of breathing based on linguistic content and/or prosodic features of the speech. The trained model may be used to estimate the respiratory sensor values of a speech signal in real time to predict the respiratory signal (and hence provide enough time for a ventilator to react to deliver gas for the time of inspiration). The results indicated above demonstrate that the model 302 can be trained to provide sufficient sensitivity and/or precision to enable a ventilator to adequately meet a subject's respiratory needs while the subject is speaking and/or to support the subject during speech.

In another embodiment, the recurrent neural network, RNN, is replaced by a convolutional neural network, CNN. Based on the same training and test data as described in the above embodiment, the CNN was found to predict the respiratory signal with a correlation of 0.41 and mean square error of 0.00229 to the actual respiratory signal. In another embodiment, a memory network such as described above may employ an attention mechanism, multi-task learning-based approach with breathing rate (e.g., the rate of breathing in and out) as an auxiliary training parameter for improved estimation of the predicted respiration signal.

Figure 5:
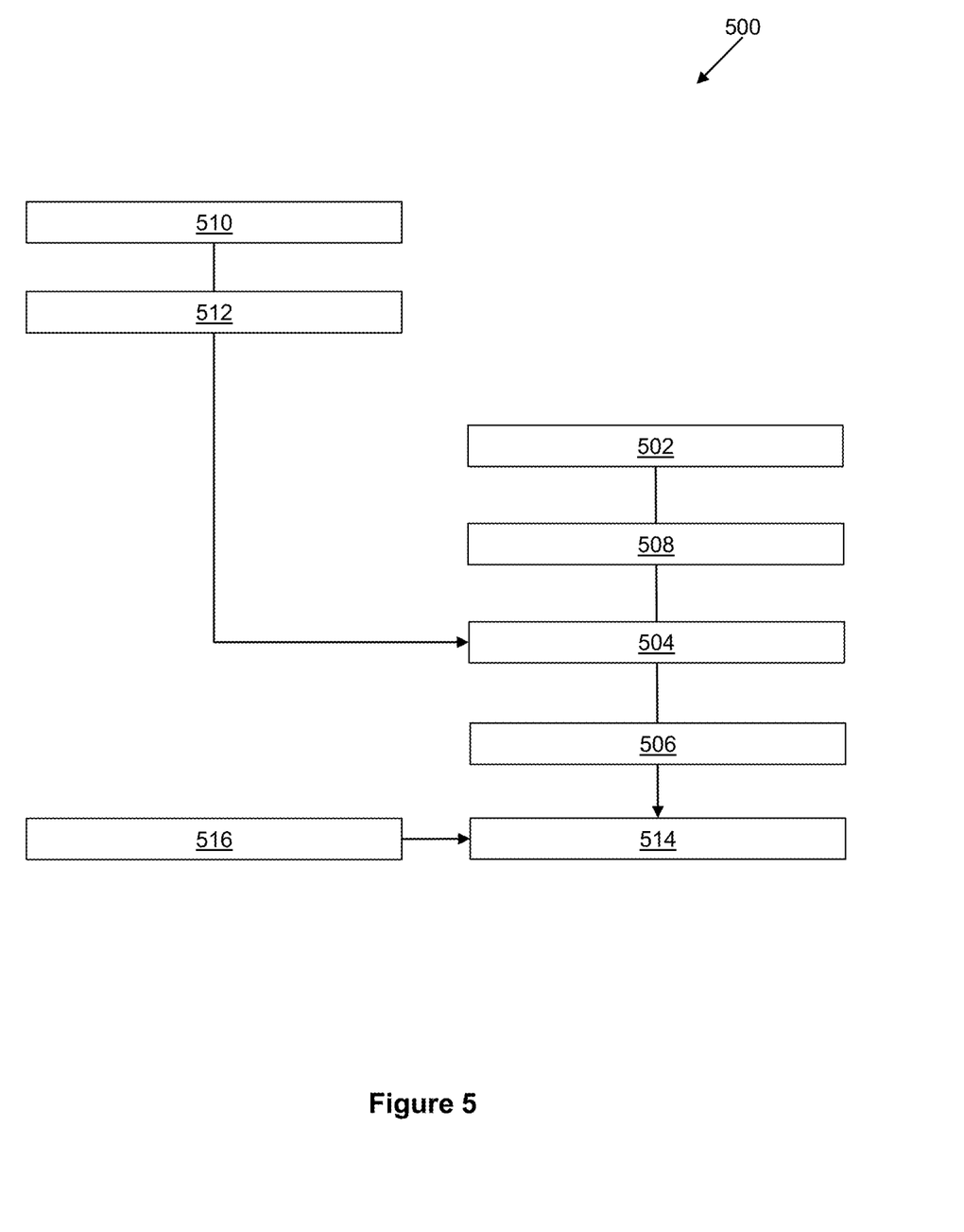
FIG. 5 refers to a method of controlling delivery of gas according to an embodiment.

FIG. 5 is a flowchart of a method 500 of predicting a subject's breathing pattern according to an embodiment, e.g., to enable control of a ventilation system (such as described above in relation to FIG. 2) for delivering gas to the subject. Where appropriate, certain blocks described in relation to the method 500 may be omitted and/or the arrangement/order of the blocks may be modified at least partially to the arrangement/order indicated by FIG. 5. The method 500 may comprise at least one block corresponding to the method 100 of FIG. 1. For example, block 502 may correspond to block 102 of FIG. 1, block 504 may correspond to block 104 of FIG. 1 and/or block 506 may correspond to block 106 of FIG. 1. Thus, the method 500 may be implemented in conjunction with and/or comprise the method 100 of FIG. 1. Further, the method 500 may be implemented by or in conjunction with certain modules or blocks such as described in relation to certain apparatus and systems described herein (e.g., as depicted by FIGS. 2 and/or 3). Certain blocks described below may therefore make reference to certain features of other figures described herein.

The method 500 comprises, at block 508, deriving a respiration signal from the indication. The respiration signal is used as an input to the machine learning model. The machine learning model may be used to predict (e.g., using processing circuitry), the time of inspiration by the subject.

As mentioned previously, a plurality of trainers may be used to train the machine learning model (e.g., the machine learning model 302 of FIG. 3). In this regard, the machine learning model may be built using a neural network configured to identify, at block 510, any correlations between a speech signal and a corresponding respiration signal acquired from a plurality of trainers. Where any correlations are identified, these correlations may be used to update the network weights of the neural network to improve the predictions made based on the neural network. By using the neural network, the potentially large volume of training data used as an input to the neural network may be analyzed to identify difficult-to-spot patterns in the speech data so as to improve predictions of the respiration signal without having to use a predetermined model (i.e., based on a human analyst's assumptions) which could be subject to bias and/or make erroneous assumptions about certain correlations.

The neural network may be configured to identify, at block 512, at least one of: linguistic content and/or prosodic features of speech signals acquired from the trainers to facilitate identification of the correlation. Linguistic content and/or prosodic features of speech signals may be indicative of the context of the speech, which may be useful for determining certain correlations that may not otherwise be straightforward to identify without using a machine learning approach. For example, linguistic content of speech signals may comprise a significant amount of information with potentially complex and variable speech patterns such that it may be difficult for a human analyst to identify a model that makes sufficiently reliable predictions.

The method 500 comprises causing, at block 514, a ventilation system (such as described previously) to deliver the gas to the subject during the predicted time of inspiration for a specified period of time. The specified period of time may be one of: a pre-determined period of time; or adapted according to the subject's individual needs. The start point for the specified period of time may begin upon activation of a ventilator. The specified period of time may indicate the duration of time over which gas is to be delivered to the subject. The specified period of time may or may not correspond to the predicted duration of inspiration. For example, if there is any lag due to the reaction time of the ventilator, the specified period of time may be longer than the inspiration to take into account the lag.

Where the specified period of time is adapted according to the subject's individual needs, these needs may be determined, at block 516, based on at least one of: linguistic context of the subject's speech; previous inspiration durations by the subject; and a medical need of the subject. For example, a determination may be made based on the linguistic context of the speech and/or previous inspiration durations that the subject is speaking in sentences and, if the subject is predicted to inspire between the sentences (or at any other point) for a certain duration, the specified period of time may be adapted accordingly. Further, if the subject has a particular medical need (e.g., a target oxygen level in their lungs or any other medical need), the specified of time may be adapted accordingly to provide sufficient gas (e.g., to reach the target oxygen level).

Although not depicted in FIG. 5, the method 500 may comprise using change-point detection (such as described above) to predict the time of inspiration of the subject based on the subject's respiration signal as predicted by the machine learning model based on the speech pattern of the subject.

Figure 6:
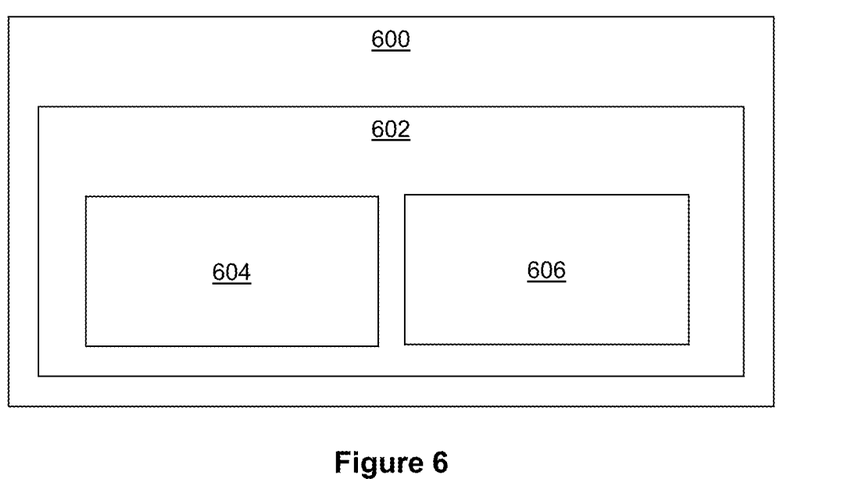
FIG. 6 is a schematic drawing of an apparatus for controlling delivery of gas according to an embodiment.

FIG. 6 is a schematic illustration of apparatus 600 according to an embodiment for implementing certain methods described herein. Where appropriate, the apparatus 600 is described in relation to the certain components of FIG. 2 for ease of reference. The apparatus 600 comprises processing circuitry 602 which may, for example, be implemented in at least one of the prediction module 210 and ventilator 208 of FIG. 2.

The processing circuitry 602 comprises a prediction module 604 which may at least partially implement certain methods described herein such as described in relation to FIGS. 1 and/or 5 and/or at least partially provide the functionality described in relation to the systems of FIGS. 2 and/or 3. In this embodiment, the prediction module 604 is configured to use an indication of a speech pattern of a monitored subject to determine a predicted time of inspiration by the subject based on a machine learning model for predicting a relationship between the speech pattern and a breathing pattern of the subject.

The processing circuitry 602 further comprises a control module 606 which may implement certain methods described herein such as described in relation to FIGS. 1 and/or 5 and/or provide the functionality described in relation to the apparatus or systems of FIGS. 2 and/or 3. In this embodiment, the control module 606 is configured to control delivery of gas to the subject based on the predicted time of inspiration by the subject. For example, the control module 606 may generate a ventilator control signal (such as described in relation to FIG. 2) for causing a ventilator to deliver gas to the subject for the time of inspiration by the subject. In some embodiments, the apparatus 600 may form part of a ventilator such as described above in relation to FIG. 2. In some embodiments, the apparatus 600 may be a separate entity (e.g., a separate computer, server, or the like) communicatively coupled to the ventilator and configured to provide instructions or another indication to the ventilator so as to cause the ventilator to deliver gas at the times determined by the apparatus 600.

Figure 7:
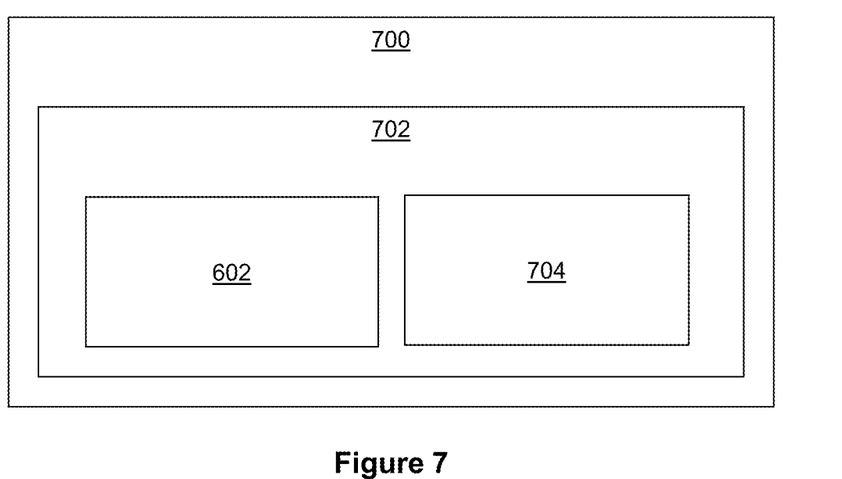
FIG. 7 is a schematic drawing of an apparatus for controlling delivery of gas according to an embodiment.

FIG. 7 is a schematic illustration of apparatus 700 according to an embodiment for implementing certain methods described herein. In this embodiment, the apparatus 700 comprises processing circuitry 702 comprising the processing circuitry 602 of FIG. 6 and a sound transducer 704 (e.g., a microphone) configured to obtain a speech signal corresponding to the speech pattern of the subject. In some embodiments, the apparatus 600 or 700 may further comprise a ventilator such as described in relation to FIG. 2.

Figure 8:
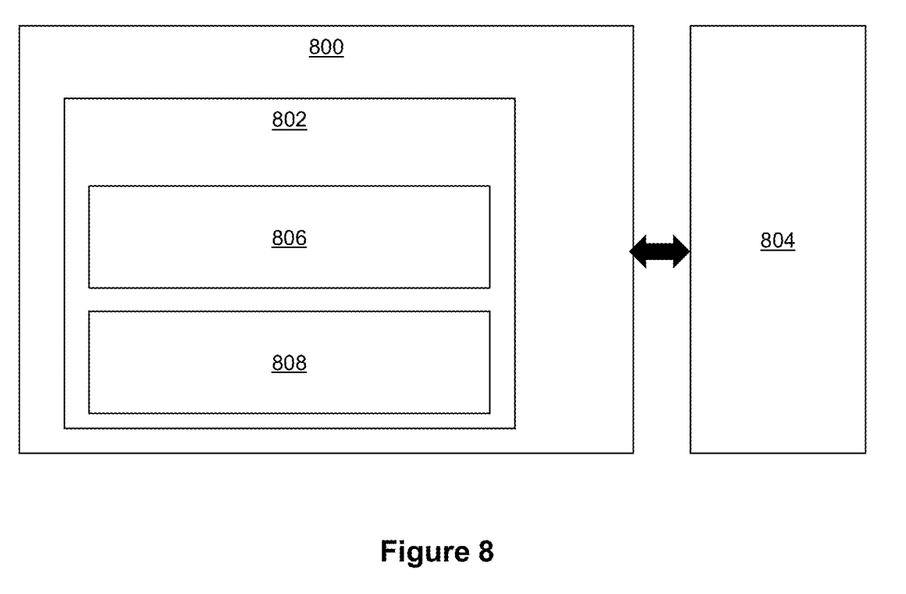
FIG. 8 is a schematic drawing of a machine-readable medium for controlling delivery of gas according to an embodiment.

FIG. 8 schematically illustrates a machine-readable medium 800 (e.g., a tangible machine-readable medium) according to an embodiment which stores instructions 802, which when executed by at least one processor 804, cause the at least one processor 804 to carry out certain methods described herein (e.g., the method 100 of FIG. 1 or the method 500 of FIG. 5). The machine-readable medium 800 may be implemented in a computing system such as a computer or server for controlling a ventilator and/or may be implemented by the ventilator itself.

The instructions 802 comprise instructions 806 to cause the at least one processor 804 to determine, from an indication of a speech pattern of a subject, a predicted time of inspiration by the subject based on a machine learning model for predicting a relationship between the speech pattern and a breathing pattern of the subject.

The instructions 802 further comprise instructions 808 to cause the at least one processor 804 to control delivery of gas to the subject based on the predicted time of inspiration by the subject.

The training of the machine learning model used to predict the time of inspiration in accordance with the instructions 802 described above is now described in more detail with reference to FIG. 3 and its associated description. As explained previously, the machine learning model may be trained with a plurality of speech signals and corresponding respiration signals acquired from a plurality of trainers.

An input to the machine learning model may comprise a spectral representation of the plurality of speech signals (e.g., from each trainer). The spectral representation may comprise the Log Mel spectrogram described above. The input may further comprise an indication of the corresponding respiration signals at specified time intervals. The indication may comprise or be indicative of the respiration signal obtained at the end of each time window selected from the training speech signal data. The input may be fed into a neural network (such as any of the neural networks described above) comprising a plurality of memory layers such that, when the neural network is optimized to update network weighting based on the input, the machine learning model is updated accordingly.

The spectral representation of each of the plurality of speech signals may be obtained by filtering each speech signal to spectrally flatten the speech signal and boost higher frequencies compared with lower frequencies of the speech signal. A Fourier transform (such as the STFT) may be applied to the spectral representation to obtain a power spectrum corresponding to the speech signal. A Mel-frequency scaling may be applied to the power spectrum to obtain a Mel spectrogram (which in some embodiments may be a Log Mel spectrogram). A plurality of time windows may be selected from the Mel spectrogram, wherein each time window is separated by a specified stride interval. In the embodiment of FIG. 3, each time window has a duration of 4 seconds and is separated from the subsequent time window by a stride of 10 milliseconds. It is within this stride interval that the indication of the corresponding respiration signals may be obtained. In other embodiments, the length of the time window and/or stride may be different to those indicated in the above embodiment.

In this embodiment, the indication of the corresponding respiration signals at specified time intervals is obtained by obtaining a respiratory inductive plethysmography, RIP, signal from the training subject. The RIP signal value is determined at the end of each time window (i.e., within the specified stride interval).

In an embodiment, the neural network may comprise at least one of: a recurrent neural network, RNN; an RNN-long short term memory, RNN-LSTM, network; and a convolutional neural network, CNN. Although as described previously, other neural networks may be used.

In an embodiment, an attention mechanism with breathing rate as an auxiliary training parameter may be used to optimize the neural network.

While the invention has been illustrated and described in detail in the drawings and foregoing description, such illustration and description are to be considered illustrative or exemplary and not restrictive; the invention is not limited to the disclosed embodiments.

One or more features described in one embodiment may be combined with or replace features described in another embodiment. For example, the methods 100, 500 of FIGS. 1 and/or 5 may be modified based on features described in relation to the systems of FIGS. 2 and/or 3, and vice versa.

Embodiments in the present disclosure can be provided as methods, systems or as a combination of machine readable instructions and processing circuitry. Such machine readable instructions may be included on a non-transitory machine (for example, computer) readable storage medium (including but not limited to disc storage, CD-ROM, optical storage, etc.) having computer readable program codes therein or thereon.

The present disclosure is described with reference to flow charts and block diagrams of the method, devices and systems according to embodiments of the present disclosure. Although the flow charts described above show a specific order of execution, the order of execution may differ from that which is depicted. Blocks described in relation to one flow chart may be combined with those of another flow chart. It shall be understood that each block in the flow charts and/or block diagrams, as well as combinations of the blocks in the flow charts and/or block diagrams can be realized by machine readable instructions.

The machine readable instructions may, for example, be executed by a general purpose computer, a special purpose computer, an embedded processor or processors of other programmable data processing devices to realize the functions described in the description and diagrams. In particular, a processor or processing circuitry, or a module thereof, may execute the machine readable instructions. Thus functional modules of the ventilation system 200 (for example, the prediction module 210, pre-processing module 214, machine learning module 216 and/or inspiration prediction module 218) and/or functional modules of the system 300 (for example, the training speech processing module 314 and/or the test speech processing module 320) and devices may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine readable instructions may also be stored in a computer readable storage that can guide the computer or other programmable data processing devices to operate in a specific mode.

Such machine readable instructions may also be loaded onto a computer or other programmable data processing devices, so that the computer or other programmable data processing devices perform a series of operations to produce computer-implemented processing, thus the instructions executed on the computer or other programmable devices realize functions specified by block(s) in the flow charts and/or in the block diagrams.

Further, the teachings herein may be implemented in the form of a computer program product, the computer program product being stored in a storage medium and comprising a plurality of instructions for making a computer device implement the methods recited in the embodiments of the present disclosure.

Elements or steps described in relation to one embodiment may be combined with or replaced by elements or steps described in relation to another embodiment. Other variations to the disclosed embodiments can be understood and effected by those skilled in the art in practising the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method comprising:
    obtaining an indication of a speech pattern of a subject;
    using the indication to determine, using processing circuitry, a predicted time of inspiration by the subject based on a machine learning model for predicting a relationship between the speech pattern and a breathing pattern of the subject; and
    controlling delivery of gas to the subject based on the predicted time of inspiration by the subject.

2. The method of claim 1, comprising deriving a respiration signal from the indication and using the respiration signal as an input to the machine learning model to predict, using the processing circuitry, the time of inspiration by the subject.

3. The method of claim 1, wherein the machine learning model is built using a neural network configured to identify any correlations between a speech signal and a corresponding respiration signal acquired from a plurality of trainers.

4. The method of claim 3, wherein the neural network is configured to identify at least one of:
    linguistic content and prosodic features of speech signals acquired from the trainers to facilitate identification of the correlation.

5. The method of claim 1, comprising causing a ventilation system to deliver the gas to the subject during the predicted time of inspiration for a specified period of time, wherein the specified period of time is one of:
a pre-determined period of time; or
adapted according to the subject's individual needs.

6. The method of claim 5, wherein the subject's individual needs are determined based on at least one of:
linguistic context of the subject's speech;
previous inspiration durations by the subject; and
a medical need of the subject.

7. The method of claim 1, comprising using change-point detection to predict the time of inspiration of the subject based on the subject's respiration signal as predicted by the machine learning model based on the speech pattern of the subject.

8. Apparatus comprising processing circuitry, the processing circuitry comprising:
a prediction module configured to use an indication of a speech pattern of a monitored subject to determine a predicted time of inspiration by the subject based on a machine learning model for predicting a relationship between the speech pattern and a breathing pattern of the subject; and
a control module configured to control delivery of gas to the subject based on the predicted time of inspiration by the subject.

9. The apparatus of claim 8, comprising a sound transducer configured to obtain a speech signal corresponding to the speech pattern of the subject.

10. A tangible machine-readable medium storing instructions which, when executed by at least one processor, cause the at least one processor to:
determine, from an indication of a speech pattern of a subject, a predicted time of inspiration by the subject based on a machine learning model for predicting a relationship between the speech pattern and a breathing pattern of the subject; and
control delivery of gas to the subject based on the predicted time of inspiration by the subject.

11. The tangible machine-readable medium of claim 10, wherein the machine learning model is trained with a plurality of speech signals and corresponding respiration signals acquired from a plurality of trainers.

12. The tangible machine-readable medium of claim 11, wherein an input to the machine learning model comprises:
a spectral representation of the plurality of speech signals; and
an indication of the corresponding respiration signals at specified time intervals, and
wherein the input is fed into a neural network comprising a plurality of memory layers such that, when the neural network is optimized to update network weighting based on the input, the machine learning model is updated accordingly.

13. The tangible machine-readable medium of claim 12, wherein:
the spectral representation of each of the plurality of speech signals is obtained by:
filtering each speech signal to spectrally flatten the speech signal and boost higher frequencies compared with lower frequencies of the speech signal;
applying a Fourier transform to obtain a power spectrum corresponding to the speech signal;
applying a Mel-frequency scaling to the power spectrum to obtain a Mel spectrogram; and
selecting a plurality of time windows from the Mel spectrogram, wherein each time window is separated by a specified stride interval, and wherein:
the indication of the corresponding respiration signals at specified time intervals is obtained by:
obtaining a respiratory inductive plethysmography, RIP, signal from the training subject; and
determining an RIP signal value at the end of each time window within the specified stride interval.

14. The tangible machine-readable medium of claim 12, wherein the neural network comprises at least one of:
a recurrent neural network, RNN;
an RNN-long short term memory, RNN-LSTM, network; and
a convolutional neural network, CNN.

15. The tangible machine-readable medium of claim 12, wherein an attention mechanism with breathing rate as an auxiliary training parameter is used to optimize the neural network.

* * * * *